United States Patent
Godara et al.

(10) Patent No.: US 9,675,408 B2
(45) Date of Patent: Jun. 13, 2017

(54) ELECTROSURGICAL DEVICE AND METHODS

(71) Applicant: Kyphon SARL, Neuchatel (CH)

(72) Inventors: Neil Godara, Milton (CA); Jason Woo, Vaughan (CA); Emily Won, Toronto (CA); Michael Gofeld, Seattle, WA (US)

(73) Assignee: Kyphon SÀRL, Neuchâtel (CH)

( * ) Notice: Subject to any disclaimer, the term of this patent is extended or adjusted under 35 U.S.C. 154(b) by 0 days.

(21) Appl. No.: 14/985,687

(22) Filed: Dec. 31, 2015

(65) Prior Publication Data

US 2016/0113704 A1  Apr. 28, 2016

Related U.S. Application Data

(60) Division of application No. 13/660,353, filed on Oct. 25, 2012, now Pat. No. 9,241,760, which is a
(Continued)

(51) Int. Cl.
*A61B 18/18* (2006.01)
*A61B 18/14* (2006.01)
(Continued)

(52) U.S. Cl.
CPC ............ *A61B 18/148* (2013.01); *A61B 18/14* (2013.01); *A61B 18/1402* (2013.01);
(Continued)

(58) Field of Classification Search
USPC ........................................ 606/21, 23, 41, 48
See application file for complete search history.

(56) References Cited

U.S. PATENT DOCUMENTS

| 4,674,499 A | 6/1987 | Pao |
| 6,129,726 A | 10/2000 | Edwards et al. |

(Continued)

FOREIGN PATENT DOCUMENTS

WO  2007113866  10/2007

OTHER PUBLICATIONS

International Report on Patentability for Application: PCT/CA2011/050203 dated Oct. 30, 2012.
(Continued)

*Primary Examiner* — Nicole F Johnson

(57) ABSTRACT

An electrosurgical bipolar probe with internal cooling for use in systems and methods for lesioning in bone and other tissue is disclosed. The bipolar probe includes tubular electrodes configured such that the inner surface of the electrodes are cooled, directly or indirectly, while keeping the electrodes electrically isolated. An exemplary disclosed method of using a bipolar probe having an active tip having at least two electrodes for delivering energy includes the steps of: advancing the active tip into a bone tissue; delivering energy substantially between the electrodes in a bipolar manner; and supplying cooling fluid to the active tip for internal cooling of the electrodes. Some versions of the method further include the steps of monitoring the temperature of tissue to which the energy is being delivered; and controlling the delivery of energy in suspense to the temperature of the tissue.

8 Claims, 6 Drawing Sheets

Related U.S. Application Data continuation-in-part of application No. PCT/CA2011/050203, filed on Apr. 15, 2011.

(60) Provisional application No. 61/328,118, filed on Apr. 26, 2010.

(51) Int. Cl.
 *A61B 18/00* (2006.01)
 *A61B 18/12* (2006.01)

(52) U.S. Cl.
 CPC ...... *A61B 18/1482* (2013.01); *A61B 18/1485* (2013.01); *A61B 2018/00005* (2013.01); *A61B 2018/00023* (2013.01); *A61B 2018/0044* (2013.01); *A61B 2018/00565* (2013.01); *A61B 2018/00577* (2013.01); *A61B 2018/00791* (2013.01); *A61B 2018/00797* (2013.01); *A61B 2018/126* (2013.01)

(56) References Cited

U.S. PATENT DOCUMENTS

| | | | |
|---|---|---|---|
| 6,524,308 | B1 | 2/2003 | Muller et al. |
| 7,216,001 | B2 | 5/2007 | Hacker et al. |
| 2002/0077627 | A1* | 6/2002 | Johnson ............ A61B 18/1477 606/41 |
| 2003/0093007 | A1 | 5/2003 | Wood |
| 2003/0130711 | A1* | 7/2003 | Pearson ............ A61B 18/1477 607/101 |
| 2003/0212394 | A1 | 11/2003 | Pearson et al. |
| 2004/0167517 | A1 | 8/2004 | Desinger et al. |
| 2005/0177209 | A1 | 8/2005 | Leung et al. |
| 2005/0192564 | A1* | 9/2005 | Cosman ............ A61B 18/1477 606/21 |
| 2006/0111706 | A1 | 5/2006 | Truckai et al. |
| 2007/0016185 | A1 | 1/2007 | Tullis et al. |
| 2007/0027449 | A1 | 2/2007 | Godara et al. |
| 2008/0033418 | A1 | 2/2008 | Nields et al. |
| 2008/0103504 | A1* | 5/2008 | Schmitz ......... A61B 17/320016 606/79 |
| 2009/0156981 | A1 | 6/2009 | Fay et al. |
| 2010/0049190 | A1 | 2/2010 | Long et al. |
| 2010/0152725 | A1 | 6/2010 | Pearson et al. |
| 2013/0060244 | A1 | 3/2013 | Godara et al. |

OTHER PUBLICATIONS

Restriction Requirement and Response for U.S. Appl. No. 13/660,353 received on Sep. 8, 2014.

Non-Final Office Action and Response for U.S. Appl. No. 13/660,353 received on Nov. 21, 2014.

Non-Final Office Action for U.S. Appl. No. 13/660,353 received on Apr. 6, 2015.

Restriction Requirement and Response for U.S. Appl. No. 13/643,310, mailed on Sep. 25, 2014.

Non-Final Office Action for U.S. Appl. No. 13/643,310, mailed on Dec. 15, 2014.

* cited by examiner

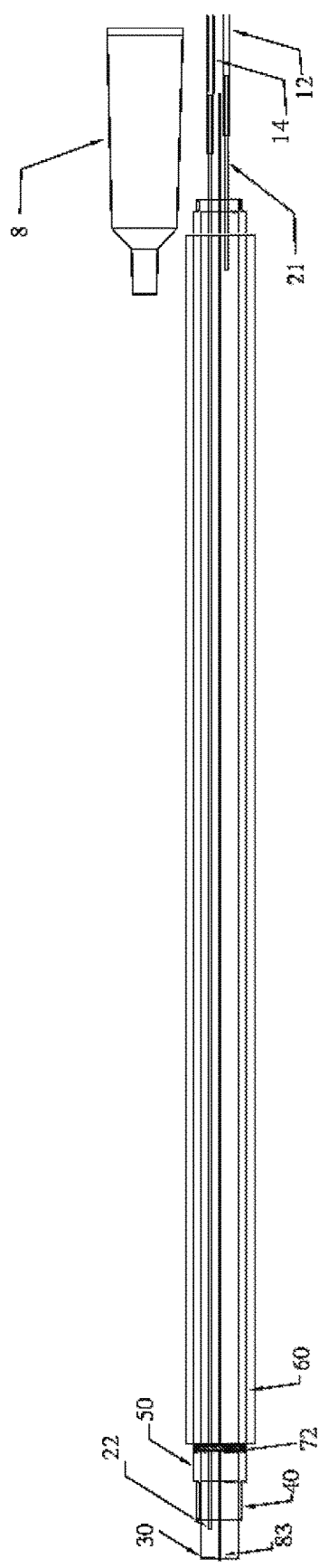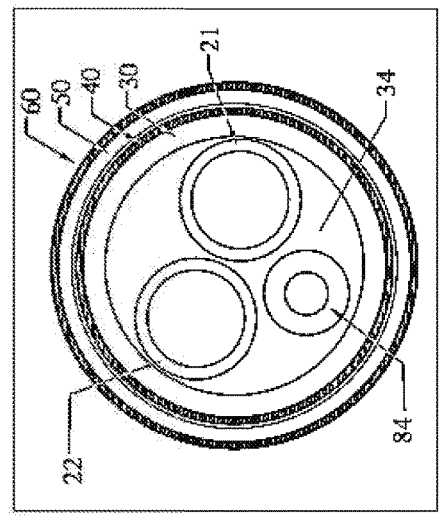
Fig. 2a
Fig. 2b

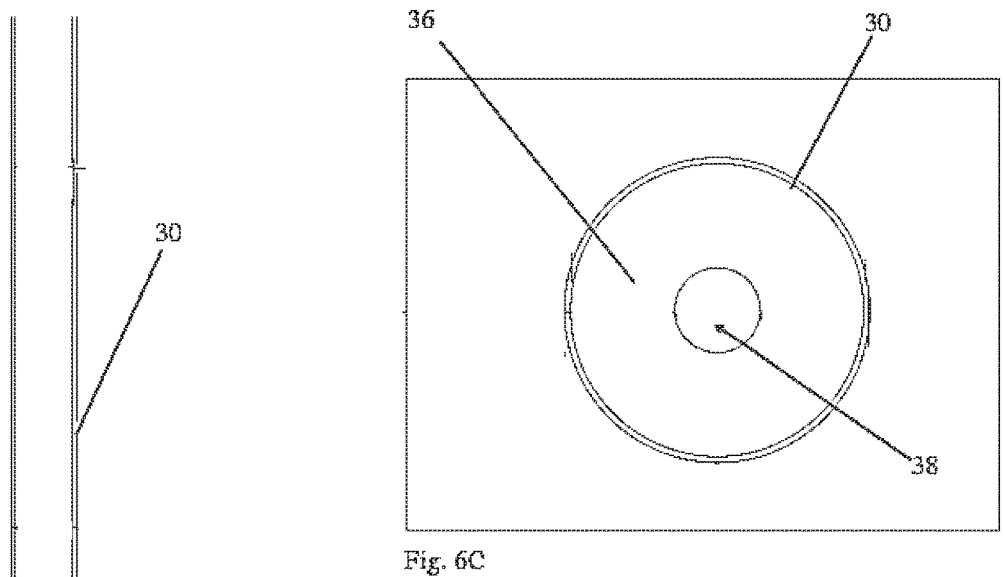
Fig. 6C
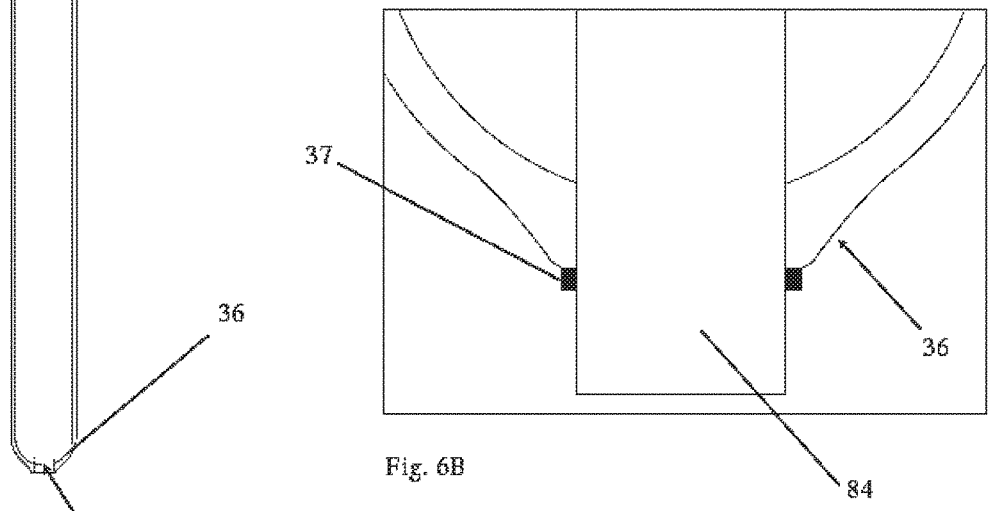
Fig. 6B
Fig. 6A

ELECTROSURGICAL DEVICE AND METHODS

CROSS-REFERENCE TO RELATED APPLICATIONS

The present application is a divisional application which claims the benefit of U.S. patent application Ser. No. 13/660,353, which is a continuation-in-part of international application PCT/CA2011/050203, filed Apr. 15, 2011, which claims the benefit of U.S. provisional patent application 61/328,118, filed on Apr. 26, 2010. All of the aforementioned applications are hereby incorporated by reference in their entirety.

TECHNICAL FIELD

The disclosure relates to an electrosurgical device. More specifically, the disclosure relates to an electrosurgical probe and methods of use thereof.

BACKGROUND OF THE ART

U.S. Pat. No. 7,918,852 to Tullis et al. is for an electrosurgical system. It discloses an electrode assembly for lesioning that includes an electrode surrounded by layers of insulation and tubing but does not disclose cooling of the lesioning electrode.

Designer et al. (U.S. Pat. No. 7,828,799) discloses a probe having two distal region electrodes with the distal electrode tip having a cone shape that extends distally. Fluid in the lumen of the probe is spaced apart from the furthest point of the distal tip electrode.

Fay et al. (pending US Publication No. 2009/0156981) discloses a flexible catheter having a plastic tip and a plastic shaft tube with electrodes attached to it.

Some prior art bi-polar probes, such as those described in U.S. Pat. No. 7,828,799 to Desinger et al. and in pending US Publication No. 2009/0156981 to Fay et al., have configurations that allow cooling fluid to contact both the active electrode and the return electrode. As cooling fluid often has some conductivity, the flow of coolant between the electrodes will cause some energy to be transmitted within the probe rather than to surrounding tissue, resulting in a loss of effectiveness and possible safety concerns. The stray energy can also affect impedance measurements, causing further problems for devices that measure impedance.

BRIEF DESCRIPTION OF THE DRAWINGS

In order that the invention may be readily understood, embodiments of the invention are illustrated by way of examples in the accompanying drawings, in which:

FIG. 2a is a side view of a probe 100, showing various features in transparency for ease of illustration, in accordance with an embodiment of the present invention;

FIG. 2b is a cross-sectional view of probe 100, taken along line 2b-2b of FIG. 2a, in accordance with an embodiment of the present invention;

FIGS. 6a, 6b and 6c are illustrations of a portion of a probe 100, in accordance with an embodiment of the present invention.

DETAILED DESCRIPTION

Figure 1:
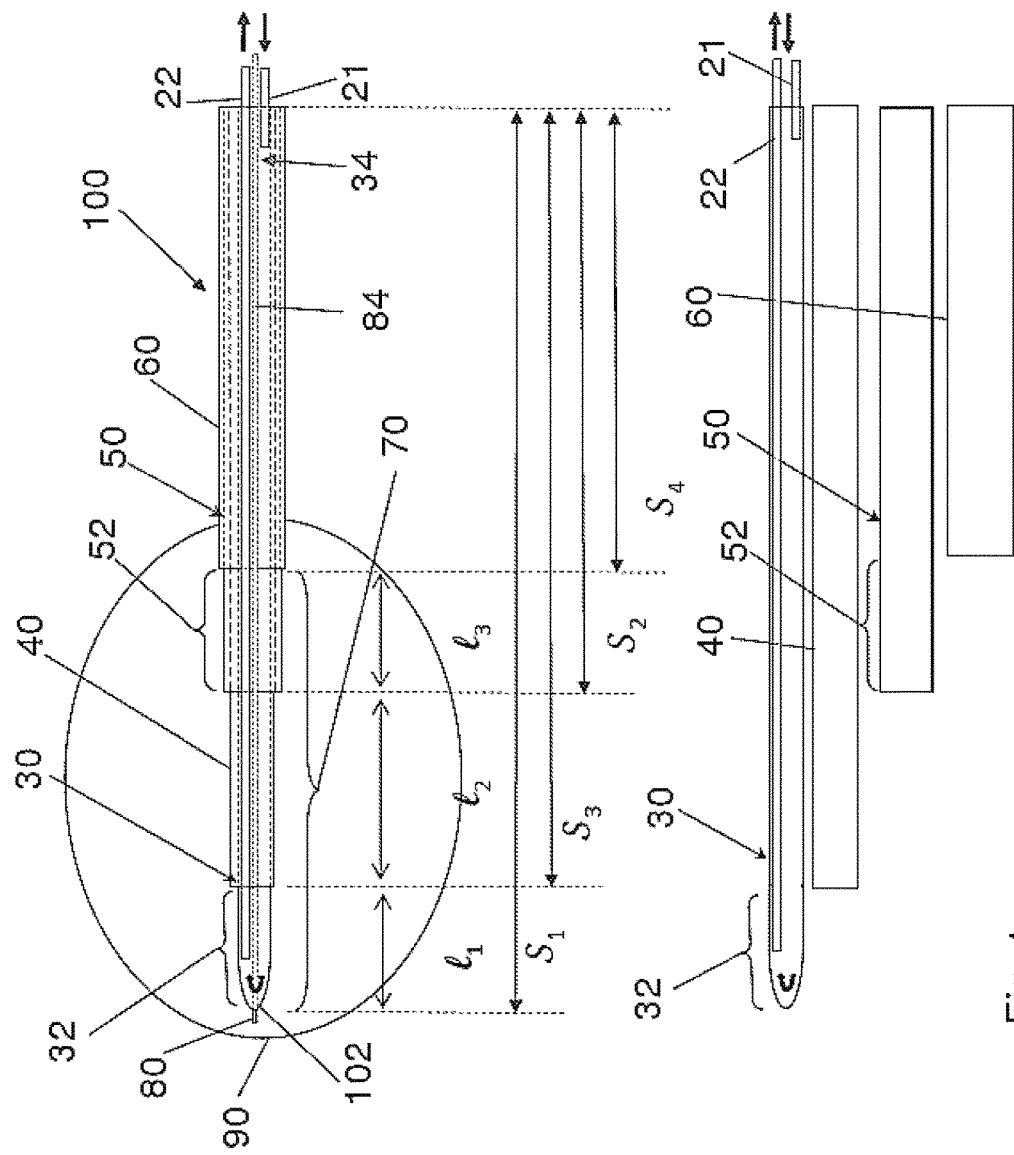
FIG. 1 is illustration of a probe 100 in accordance with an embodiment of the present invention.

Radiofrequency-based devices are often used to create lesions in soft tissues such as the liver in order to treat tumors located therein. However, creating a lesion in bone tissue using an electrosurgical device for delivering electrical energy poses unique challenges due, for example, to the electrical properties of bone. The present inventors have discovered and reduced to practice various embodiments of a unique electrosurgical probe usable to create lesions in bone suitable for reducing pain and for reducing tumor burden.

In particular, inventors have discovered that an electrosurgical probe structured to confine delivery of energy at its active tip (i.e. without requiring energy to flow to a grounding pad on the surface of a body) is particularly useful in such situations. Furthermore, a bipolar probe used for lesioning in tissue can be cooled in order to increase the efficacy of energy delivery and lesion formation. More specifically, the probe may be internally cooled by including tubular electrodes configured such that the inner surface of each electrode is cooled while keeping the electrodes electrically isolated.

Some particular embodiments allow for cooling of more than one electrode while substantially confining the coolant to a lumen formed by one of the electrodes. Thus, for example, embodiments of the present invention include an electrosurgical probe comprising at least two electrically isolated conductors and a lumen for circulating a cooling fluid within only one of said at least two electrically isolated conductors, such that only one of the conductors is directly cooled by the cooling fluid. The cooling fluid circulating within the one conductor nonetheless functions to reduce the temperature of the at least two electrically isolated conductors.

The probe can include a means for temperature monitoring which is particularly advantageous when used, for example, in tissue that hinders the predictability of lesioning such as electrically insulative tissue.

As used herein, the term "bipolar probe" is understood to mean a probe that includes at least two electrically isolated electrodes whereby energy may be delivered between those electrodes in a manner which substantially confines the energy to an area substantially surrounding the active tip and obviates the need for a grounding pad or return electrode on the surface of a patient's body, thereby avoiding a flow of electrical energy through the patient's body from the active tip to such a grounding pad. Although the term "bipolar" is used herein, it should be understood to include other forms of energy delivery whereby energy flows substantially between electrodes located on the probe and not to a grounding pad on the surface of the patient's body.

In a first broad aspect of the invention, embodiments of a method of lesioning in bone are described, the method using a bipolar probe having an active tip comprising at least two electrodes for delivering energy, the method comprising the steps of: advancing the active tip into a bone tissue; delivering energy substantially between the at least two electrodes in a bipolar manner; and supplying cooling fluid to the active tip for internal cooling of the at least two electrodes. Some embodiments of the method further comprise the steps of monitoring the temperature of tissue to which the energy is being delivered; and controlling the delivery of energy in response to the temperature of the tissue to which the energy is being delivered.

In some embodiments of the first broad aspect, the bone is a vertebral body. In some such embodiments the energy is delivered to nervous tissue at a bone-tumor interface.

In embodiments of the first broad aspect wherein the bone is a vertebral body, the method comprises the further steps of: the probe being inserted into a vertebral body at a first target location to the right of a mid-saggital plane at an angle of about 15 to about 25 degrees to the mid-saggital plane and energy is delivered to form a first bipolar lesion at the first target location within the vertebral body; and the probe being inserted at a second target location to the left of the mid-saggital plane at an angle of about 15 to about 25 degrees from the mid-saggital plane and energy is delivered to form a second bipolar lesion at the second target location within the vertebral body.

In certain embodiments, the method comprises the active tip being advanced the into a trabecular bone. In some such embodiments an introducer assembly, comprising a cannula with a stylet disposed therein, is used to advance the probe into the vertebral body, and wherein the stylet is withdrawn from the cannula subsequent to the introducer assembly being advanced into the vertebral body.

In further embodiments using an introducer assembly, the introducer assembly is inserted into the vertebral body using a transpedicular approach. In some such embodiments, the introducer assembly is inserted through a pedicle at an angle of about 15 to about 25 degrees oblique to a mid-saggital plane.

In some such embodiments using an introducer assembly, the introducer assembly is inserted into the vertebral body using a lateral approach.

In particular embodiments of the method of the first broad aspect, the energy delivered to tissue is radiofrequency energy. In some embodiments, the temperature of the tissue is maintained at between about 40 degrees and about 100 degrees Celsius. In some embodiments, energy is delivered at power levels between about 1 Watt and about 20 Watts. In some embodiments, the energy is delivered for between about 2 minutes to about 30 minutes while, in alternate embodiments, the energy is delivered for less than about 2 minutes or for more than about 30 minutes. In some embodiments, the energy is delivered such that the temperature of the tissue increases at a ramp rate from about 10° C./min to about 80° C./min.

In some specific embodiments of the first broad aspect, the method further comprises reversing the polarity of the energy to the at least two electrodes.

In some such embodiments, the method further comprises: delivering a stimulation pulse of energy, comprising a continuous train of biphasic waves at a set frequency, to the probe; navigating the active tip through the bone tissue while delivering the stimulation pulse; reversing the polarity of the at least two electrodes while delivering the stimulation pulse to identify which electrode a stimulated nerve is in proximity to; and repeating the steps of delivering a stimulation pulse, navigating the active tip and reversing the polarity, until a location of the nerve is determined.

Furthermore, in some such embodiments, the method further comprises each probe being active for about 50 percent of the time.

Some embodiments further comprise: placing at least one external temperature sensor at a boundary of a desired lesion; monitoring the at least one external temperature sensor during energy delivery; and determining lesion completion when the external temperature reaches a predefined value.

In some embodiments of the first broad aspect, a temperature selected for the cooling fluid is from about 0 degrees C. to about 30 degrees C. Some such embodiments further comprise adjusting a flow rate of the cooling fluid.

In some embodiments of the first broad aspect, the energy is delivered to a nerve within a vertebral body. In some such embodiments the energy is delivered to a basivertebral nerve.

A second broad aspect of the invention is for embodiments of a method of treating pain generated by nervous tissue at an interface between bone of a vertebral body and a tumor located at least partially within the vertebral body. The method comprises: delivering energy to the nervous tissue using a single bipolar probe having an active tip comprising at least two electrodes, the energy being sufficient to limit generation of pain signals by the nervous tissue; and cooling the at least two electrodes as energy is being delivered to the nervous tissue to limit charring of the tissue at the surface of the at least two electrodes.

With specific reference now to the drawings in detail, it is stressed that the particulars shown are by way of example and for purposes of illustrative discussion of certain embodiments of the present invention only. Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Creating predictable lesions in insulative tissue such as bone can be aided by using a bipolar probe with internal cooling. Embodiments of such a probe include tubular electrodes configured such that the inner surface of each electrode is cooled, directly or indirectly, while keeping the electrodes electrically isolated. One possible configuration is an electrosurgical probe comprising two electrically isolated electrical conductors with an inner one of the conductors inside of the other and the inner electrical conductor defining a lumen for the circulation of a cooling fluid inside of it. The probe also has an electrical insulator layer between the electrical conductors for electrically isolating the electrical conductors. The electrical insulator has sufficient thermal conductivity to allow for cooling of the outside electrical conductors by cooling fluid circulating within the lumen of the inner electrical conductor. Thus, only one conductor is cooled directly, i.e. with contact of the cooling field, while the other conductor is indirectly cooled.

FIG. 1 is an illustration of a probe 100, in accordance with an embodiment of the present invention. The probe comprises an inner elongate conductor 30 and an outer elongate conductor 50. The inner and outer conductors 30, 50 each have a hollow tubular configuration and define a lumen there-through. The inner and outer conductors 30, 50 are coupled to an energy supply at proximal ends thereof. In one example, the energy supply may comprise a radiofrequency (RF) energy delivery source and an energy sink. In one specific example, the inner conductor 30 functions as an active electrode and is coupled to an RF energy delivery source, and the outer conductor 50 is coupled to an energy sink such as a ground connection, forming a return electrode. In other words the inner conductor 30 functions as a control electrode and the outer conductor 50 functions as a neutral or ground reference electrode. In another example, the outer conductor 50 functions as an active electrode and the inner conductor 30 functions as a return electrode. In such embodiments, probe 100 can be operated in a bipolar manner, where energy is delivered substantially between conductors 30, 50. The inner and outer conductors 30, 50 may be connected to the RF energy delivery source and ground via an electrical connection through a probe handle 8, shown in FIG. 2a, which may be coupled to a proximal end of probe 100. The inner conductor 30 is disposed coaxially within the lumen of the outer conductor 50. The inner and the outer conductors 30, 50 each comprise an electrically conductive portion at least along a length thereof and more specifically, at least along a distal segment of conductors 30, 50. Each of the electrically conductive portions are coupled to an energy supply through an electrically conductive pathway.

In FIG. 1, the inner conductor 30 and the outer conductor 50 are electrically conductive along their length. In one example as shown in FIG. 1, the inner conductor 30 has a length S1, and the outer conductor 50 has a length S2. In one example, the inner and the outer conductors, 30 and 50, each comprise a stainless steel hypotube. In another example, the inner and outer conductors 30, 50 may comprise an electrically conductive, biocompatible material such as titanium or nitinol. The inner conductor 30 is electrically isolated from the outer conductor 50 by an inner insulator 40 disposed between the inner conductor 30 and the outer conductor 50. In some embodiments, the inner insulator 40 extends longitudinally along at least the entire length of the outer conductor 50. In some embodiments, it has a length that is greater than the length of the outer conductor 50. In one example, as shown in FIG. 1, the inner insulator has a length S3 that is greater than length S2 of the outer conductor 50. In some embodiments, the inner insulator 40 is electrically insulative and thermally conductive. In the illustrated embodiments, the distal most portion of the inner conductor 30 is exposed at the distal tip thereof and forms a distal electrode 32 having a length L1.

The inner elongate conductor 30 as shown in FIG. 1 and FIG. 2b has a closed distal end thereof and defines a lumen 34 there-through for circulating a cooling fluid. The term "circulate" relates to fluid that mostly moves or is caused to move through a generally closed system in a controlled manner rather than fluid that enters and mostly passes through the system to the outside environment such as passing through an open ended tube. A fluid inlet tube 21 may be disposed within the lumen 34 to supply cooling fluid within the inner lumen 34 from a cooling supply (not shown). A fluid outlet tube 22 may be disposed alongside the fluid inlet tube 21 within the inner lumen 34 to allow the cooling fluid to exit via a proximal end of the probe 100. The fluid outlet tube 22 may extend along a majority of the length of the inner conductor 30. In some embodiments, fluid outlet tube 22 may be shorter than fluid inlet tube 21. The outer conductor 50 has an insulator 60 that is electrically insulative disposed on an outer surface thereof, along at least a portion of the outer conductor 50, whereas a distal portion of the outer conductor 50 remains electrically exposed, forming a proximal electrode 52 with a length L3. In one example, the outer insulator 60 has a length S4 as shown in FIG. 1. In one embodiment the outer insulator 60 may have a length that is substantially the same as the length of the outer conductor 50. The inner insulator 40 is exposed between the distal edge of the proximal electrode 52 and the proximal tip of the distal electrode 32. The length of the exposed insulator is labelled as L2. The region of the probe extending from the proximal electrode 52 to the distal electrode 32 forms an active tip 70. A radiopaque band 72 may be positioned at a proximal end of the active tip 70 as shown in FIG. 2a. The radiopaque band 72 may act as a navigational reference to guide and facilitate in positioning of the active tip 70 at a target location within a patient's body. In other embodiments, the radiopaque band may be positioned at any location along the active tip 70 or at any location along the probe 100. In still another embodiment, more than one radiopaque band 72 or a radiopaque marker may be positioned along the probe. In one example the radiopaque band 72 may function as a navigational reference under fluoroscopic imaging.

In one example, the proximal electrode 52 is a return electrode and the cooling fluid cools the proximal electrode 52 prior to reaching and cooling the distal electrode 32, which is the active electrode. This may provide a more uniform lesion to be produced when RF energy is supplied to the probe 100. The structure of the probe 100, in one example, allows cooling fluid to indirectly cool the proximal electrode 52 and to directly cool the distal electrode 32. The cooling fluid flows through the inner lumen 34 of the inner conductor 30 and coaling is transmitted indirectly to the proximal electrode 52 through thermal conductivity through a wall of the inner conductor 30 and a wall of the inner insulator 40. Cooling fluid is supplied from the fluid inlet tube 21 which exits into the lumen 34 near the location of the proximal electrode 52. The relatively low temperature of the cooling fluid cools proximal electrode 52 indirectly, thus raising the temperature of the fluid. In other words, the cooling fluid allows heat to be removed from the proximal electrode 52. The fluid then flows within the lumen 34 to the distal electrode 32 at the slightly elevated temperature. Thus, cooling fluid at a lower temperature is used to indirectly cool the proximal electrode 52, whereas, cooling fluid that is at a slightly higher temperature passes through the distal electrode 32 to cool it directly. It is possible that by cooling proximal electrode 52 indirectly at a lower temperature and cooling the distal electrode 32 directly at a slightly higher temperature, cooling of electrodes 32, 52 will be substantially equivalent. This may allow cooling to be transmitted uniformly to both the proximal and distal electrodes 52, 32, thus allowing a relatively uniform heat distribution around the two electrodes. This may allow a more uniform lesion to be produced when the electrodes 32, 52 are placed in target tissue. Providing cooler fluid to cool the proximal electrode 52 may offset the difference in cooling at the proximal and distal electrodes 52, 32 due to direct and indirect cooling respectively.

In the case of the embodiment of FIG. 1, another factor that can help compensate for distal electrodes 32 being directly cooled while proximal electrode 52 is indirectly cooled is that proximal electrode 52 has a larger diameter and circumference. Consequently, for distal and proximal electrodes of equal length, proximal electrode 52 will have a slightly larger inner surface, which will increase the effectiveness of the internal cooling fluid.

In one example, the cooling fluid may comprise water. In another example, the cooling fluid may comprise saline. In an alternate example an alcohol may be used. As a further example, an isopropyl alcohol may be used. In one embodiment the temperature of the cooling fluid may range from about its freezing point to about room temperature. In one embodiment, the fluid inlet and outlet tubes, 21, 22 may be constructed from a metal. In one example the fluid inlet and outlet tubes are made from stainless steel hypotubes and may be connected to the fluid supply at proximal ends thereof with non-conductive supply tubes 12, 14. These may comprise any non-conductive material such as a polymer. In one specific example, the supply tubes 12, 14 comprise of Polyvinylchloride (PVC) tubing that may be UV (ultraviolet) glued to the stainless steel inlet and outlet tubes 21, 22. In other embodiments, any other means can be used to join the supply tubes to the outlet tubes. In other embodiments the fluid inlet and outlet tubes 21, 22 may be constructed from a non-conductive material such as a polymer. In still other embodiments, the fluid inlet and outlet tubes 21, 22 may be formed of alternate materials. The fluid inlet and outlet tubes 21 and 22 may be positioned alongside each other within the inner lumen 34 of the inner conductor 30. In other embodiments any flow pathway may be provided to the probe 100 to allow fluid to enter the inner conductor 30 and exit thereform. The flow pathway may comprise a fluid inflow path that is separate from a fluid outflow path which provides directional flow. In some embodiments cooling fluid may be directed into the inner conductor 30 directly without use of the fluid inlet tube 21.

In one embodiment the active tip 70 may have a length (L1+L2+L3) that ranges from about 5 mm to about 40 mm. In one example, the length of the distal electrode 32 (L1), the exposed inner insulator 40 (L2), and the proximal electrode 52 (L3) may vary in about a 2:1:2 ratio. In other embodiments the ratio may be in about a 1:1:1 configuration. Alternate embodiments am possible as well. In other embodiments, the lengths L1, L2 and L3 may have a different ratio. In another example, the L1:L2:L3 ratio is about 7:6:7.

Figure 5:
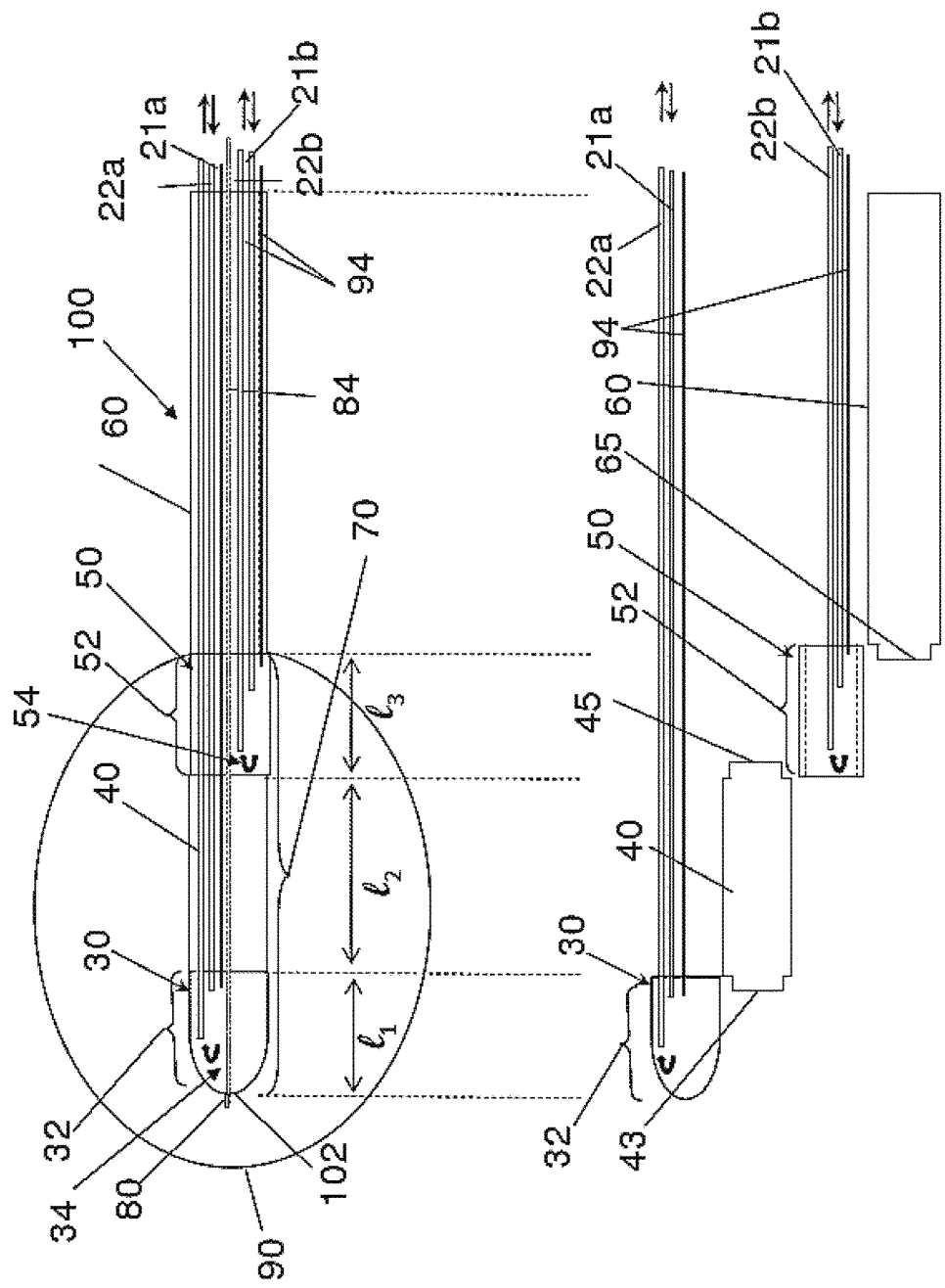
FIG. 5 is an illustration of a probe 100, in accordance with an alternate embodiment of the present invention.

In another embodiment, the inner and outer conductors 30, 50 may only extend along a portion of the probe 100. In one example inner and outer conductors 30, 50 may be electrically conductive along their lengths thereof and may form the proximal and the distal electrodes, 32 and 52. In one specific example, as shown in FIG. 5, only the exposed portions of the inner and outer conductors 30 and 50 are electrically conductive and the inner and outer conductors 30, 50 may have substantially the same width. The inner and outer conductors may be spaced apart and electrically isolated from each other by an inner insulator 40. In one example the inner insulator 40 may comprise a polymer. In a specific example, the insulator 40 may comprise a substantially rigid plastic insert. In one example the electrically isolated distal and proximal electrodes 32 and 52, may be cooled through separate cooling sources. As shown in FIG. 5, the distal electrode 32 is supplied with a cooling fluid through fluid inlet and outlet tubes 21*a* and 22*a*. Whereas, cooling to the proximal electrode 52 is supplied through cooling inlet and outlet tubes 21*b* and 22*b*. The fluid inlet and outlet tubes may comprise a non-conductive material such as a polymer. Each of the proximal and distal electrodes 52, 32 are coupled to an energy supply through electrically conductive insulated wires 94.

In this example, the distal and proximal electrodes 32 and 52 each define a closed inner lumen 34 and 54 respectively within which cooling fluid flows. The distal electrode 32 has a closed distal end and a closed proximal end formed by co-operative engagement of the distal electrode proximal portion with a distal face 43 of the inner insulator 40, defining the closed inner lumen 34. The proximal electrode 52 has a has a closed distal end formed by co-operative engagement of the proximal electrode distal end with the proximal face 45 of the inner insulator 40 as shown in FIG. 5. The proximal electrode 52 further has a closed proximal end defined by co-operative engagement of the proximal electrode proximal end with a distal face 65 of the outer insulator 60, defining the closed inner lumen 54. The cooling fluid is restricted within the lumens 34 and 54. The distal face 65 of the outer insulator, as well as the distal face 43 and the proximal face 45 of the inner insulator, extend substantially transversally along the width of the probe. The distal face 65 may comprise openings to allow fluid inlet tubes 21*a*, 21*b* and fluid outlet tubes 22*a*, 22*b* as well as insulated wires 94 to extend therethrough. Similarly, distal and proximal faces 43 and 45 may provide openings therethrough to allow passage of the inlet and outlet tubes 21*a* and 21*b* respectively and one of the insulated wires 94. A seal may be provided around the openings to ensure that cooling fluid is restricted within the lumens 34 and 54.

Additionally, a temperature sensor 80 may be positioned at a location along the probe 100 as shown in FIGS. 1, 2 and 5. In one embodiment the temperature sensor 80 may be positioned substantially adjacent the distal tip 102 of the probe 100. For example, the temperature sensor 80 may protrude from the surface of the distal electrode 32. In other words temperature sensor 80 may jut out or stick out from a surrounding surface of the probe 100. In other embodiments the temperature sensor 80 may be positioned at any location along the length of the probe. In some embodiments the temperature sensor 80 may be positioned at or adjacent to the active tip 70. In one example, the temperature sensor 80 may comprise a thermocouple. In one specific example, a thermocouple may be formed using a hypotube 84 disposed within the lumen 34 of the inner conductor 30. A constantan wire can be disposed within the thermocouple hypotube 84 to form a thermocouple junction 83 about the distal tip 102, as shown in FIG. 2*a*. In other embodiments, a thermocouple may be formed using a pair of wires to form a junction. In one example, a thermocouple is positioned at a distal face of the proximal electrode 52. In another example, a thermocouple is positioned between the proximal electrode 52 and inner insulator 40. In one example, the temperature sensor 80 is coupled to and in communication with a controller for the energy supply, for example the energy supply having an RF energy delivery source. In one example, the temperature sensor 80 may be coupled to a controller at its proximal end via the handle 8.

In some embodiments a second temperature sensor is proximate to proximal electrode 52 and is in communication with a controller for the energy supply for providing additional information. Such an embodiment could be used with a generator capable of capable of monitoring two temperature sensors at one time. Alternatively, a generator capable of monitoring only one temperature at a time could be used if an external device swapped between the two (or more) temperature sensors.

Generally, embodiments of the present invention may comprise a plurality of temperature sensors, which may be located, for example, on or adjacent to the surface of the electrodes, between the electrodes or at or near the electrodes, proximally or distally. A generator used in system with two or more temperature sensors would include an algorithm for controlling the output of energy based on multiple temperature readings.

The inner conductor 30 has a closed distal end. As shown in FIGS. 6*a*, 6*b* and 6*c*, in one embodiment, the distal end of the inner conductor 30 is swaged to form a concentrically tapered end 36 with an opening 38 therethrough. The size or diameter of the opening 38 is smaller than a diameter of the inner conductor 30 along its length as shown in FIG. 6*c*. The opening 38 allows the thermocouple hypotube 84 to extend or protrude from the distal end face of the inner conductor 30. In some embodiments, the thermocouple hypotube 84 may be laser welded to the inner conductor 30 at a wall of the opening 38. In other examples any other means of attachment may be used. In some embodiments where the thermocouple may be positioned at any other location along the probe, the distal end of the inner conductor 30 may be swaged in a similar manner as disclosed above to reduce the size of the opening at the distal end of the inner conductor hypotube 30. The reduced diameter opening may then be closed by laser welding at the distal most end. The closed distal end of the inner conductor 30 may be formed using other means. In some embodiments the closed distal end of the hypotube may comprise a separate end piece or end cap that may be attached to the distal end of the hypotube. In some examples, the end piece may be dome shaped, triangular shaped or may have a flat surface thereon. The end piece may or may not be metal. In other embodiments a closed distal end of the inner conductor may be formed by providing an end piece in the form of a metal insert which may be laser welded to the hypotube distal end. In other embodiments, any other attachment means may be used. In one example, an adhesive may be used to attach the end piece to the hypotube distal end. In one such example, the adhesive may be an ultraviolet (UV) glue.

In some embodiments, the probe size may range from an outer diameter of about 13 Gauge, 2.413 mm (0.095"), to about 17 Gauge, 1.47 mm (0.058"). In one example, the probe 100 has a diameter of about 17 Gauge and has an outer conductor 50 with a length of about 215.9 mm (8.5") and an inner conductor 30 with a length of about 228.6 mm (9.0"). The fluid outlet tube 22 has a length of about 241.3 mm (9.5") and extends into the handle, whereas the fluid inlet tube 21 is about 38.1 mm (1.5") in length and positioned at the proximal end of the inner conductor 30. The thermocouple hypotube 84 is positioned within the inner lumen 34 of inner conductor 30 and has a length of about 254 mm (10").

In one example the insulators 40 and 60 may comprise a polyester. The insulators 40 and 60 may be disposed onto the conductors 30 and 50 respectively using a heat-shrink procedure. The conductors 30 and 50 may be electrically conductive along their length. In one example, the polyester is a Polyethylene terephthalate (PET). In other embodiments a polyamide, polyimide, Fluorinated ethylene propylene (FEP) or polytetrafluoroethylene (PTFE), may be used to form one or both of the insulators 40, 60. In one embodiment the insulators 40 or 60 may be provided in the form of a coating or a layer. In still other embodiments PEEK may be used. In one example the thickness of the inner insulator 40 may vary from about 0.0127 mm (0.0005") to about 0.254 mm (0.010"). The thickness of the inner insulator 40 provides sufficient thermal conductivity allowing cooling to be conveyed to the outer conductor 50 and allow cooling of the outer conductor 50. This allows heat to be removed from the outer conductor 50. This may allow a larger lesion to be produced and minimizes charring of tissue. In one specific example, PET is used in insulators 40 and 60, each having a width of about 0.03175 mm (0.00125").

In one embodiment of a method aspect of the present invention, the probe 100 is used to treat a region within a patient's body. In one embodiment, the region may comprise tissue with varying composition. In one such embodiment, the tissue may comprise any one of or a combination of vascular tissue, soft tissue, trabecular bone tissue, cortical bone tissue, fatty tissue, tumor or nervous tissue.

Figure 3:
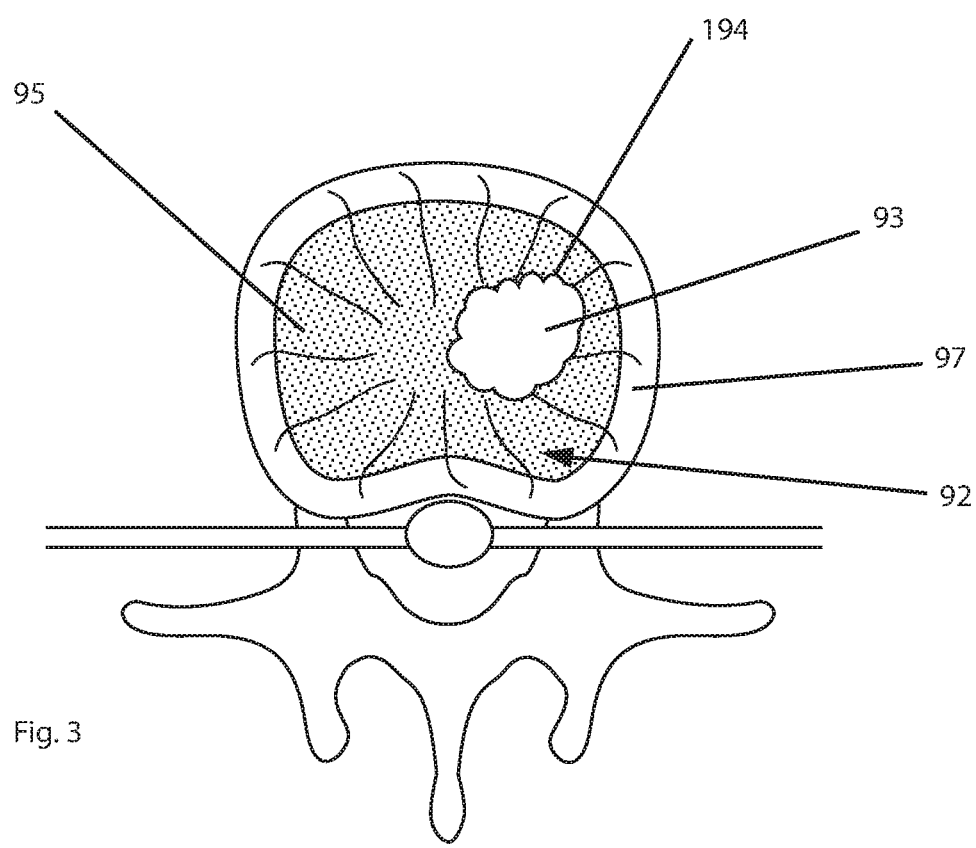
FIG. 3 is an illustration of a target location, in accordance with an embodiment of a method of the present invention.

In one specific embodiment the probe 100 is placed within a vertebral body. For example, as shown in FIG. 3, the probe 100 may be positioned adjacent a tumor 93 within a vertebral body at a bone-tumor interface 194. The probe 100 may be used to destroy nervous tissue generating pain signals at the bone-tumor interface. In one example, the probe 100 is advanced into a vertebral body 92 until the distal end 102 of the probe is positioned at the tumor-nerve interface at the edge of the tumor 93 adjacent nerves 94 as shown in FIG. 3. In one specific example, the probe active tip 70 may be positioned within the trabecular bone 95 within the vertebral body 92 that is encased by the electrically insulator cortical bone 97. In one embodiment, the probe 100 is positioned substantially adjacent the rich nerve supply within the vertebral body. In one embodiment, the probe 100 may be positioned within or substantially adjacent to the vertebral body in proximity to sensitive structures such as the cortical bone that may be non-conductive or in other words may have a low electrical conductivity.

Nerve stimulation can be used to position a probe. In bipolar nerve stimulation applications, the stimulation effects are not symmetric about each electrode. One electrode will have a larger stimulation capacity for a given biphasic wave. The electrode that is closest to a stimulated nerve can be identified by manipulating (reversing the polarity). Balanced stimulation of nerves can be achieved by alternating the polarity in an balanced manner. For example, 10 pulses could be delivered with a first electrode as the control electrode to more intensely stimulate the nerves nearest to it, and then 10 pulses could be delivered with a second electrode as the control electrode. An embodiment of a method using such a procedure to help position a probe includes the steps of: emitting a stimulation pulse comprising a continuous train of biphasic waves at a set frequency, navigating the active tip through tissue, and reversing the polarity of the two electrodes to identify which electrode a stimulated nerve is in closest to.

The probe 100 may improve heating capability in the vicinity of a non-conductive structure. The probe 100 provides energy in a bipolar manner and may be used in the vicinity of a cortical bone structure or other non-conductive structures to provide treatment to the non-conductive structure through indirect thermal conduction. Thus, probe 100 may be used to treat structures that are non-conductive in monopolar RF applications, where the energy transmission to a ground may be limited as the non-conductive structure is encountered in the energy pathway to the ground.

In another example, probe 100 may be used to target nerves at other locations within the vertebral body. In still another example, the probe 100 may be positioned substantially adjacent to or in the vicinity of any other bone tissue. In yet another example probe 100 may be used to treat a highly vascular tissue such as liver. In some embodiments, the probe 100 may be used to provide uniform or consistent lesions in the vicinity of bone or variable tissue. In other words, the probe 100 may be used to provide lesions that are substantially homogeneous.

Figure 4A:
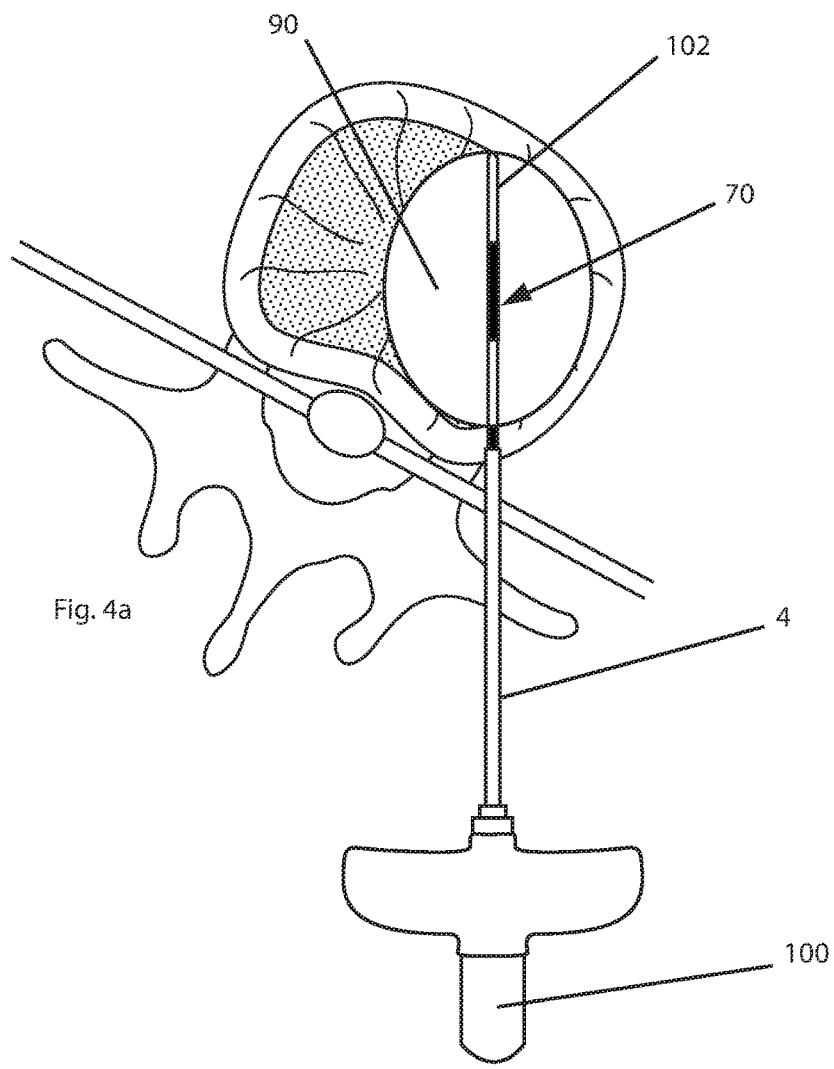
FIGS. 4a and 4b are an illustration of a method in accordance with an embodiment of the present invention.
Figure 4B:
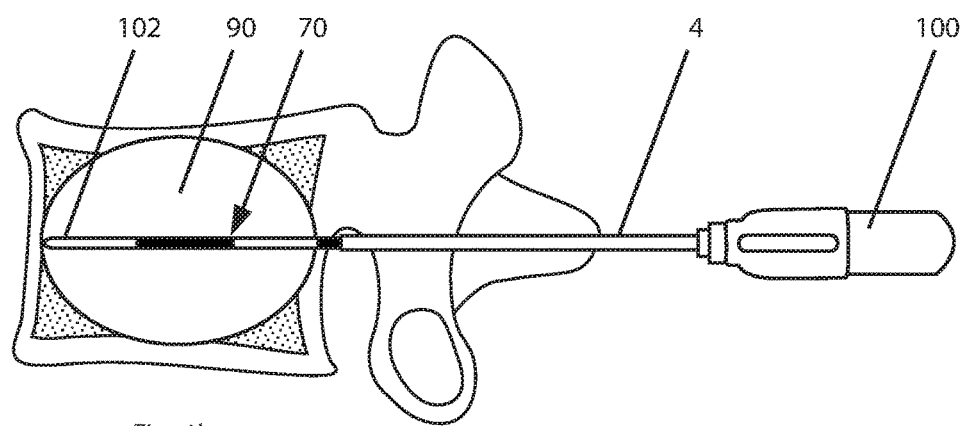

In one particular embodiment an introducer needle assembly may be inserted and advanced to a target location within a patient's body. The introducer needle assembly may comprise a cannula with a stylet disposed therein. In one example, the target location is a vertebral body as shown in FIGS. 4a and 4b. In such an embodiment, the introducer assembly 4 may be inserted into the vertebral body using a transpedicular approach. The introducer needle assembly may be inserted through the pedicle at an angle of about 15 to about 25 oblique to the mid-saggital plane, which provides a trajectory to access the vertebral body. In another embodiment a lateral approach may be used. In still other embodiments any approach that allows access to the vertebral body may be used. As an example, any conventional approach used in standard vertebroplasty or vertebral augmentation procedures to gain access to the vertebral body, may be used. Once the introducer needle assembly has been positioned at the target site, the stylet may be withdrawn from the cannula. The probe 100 may then be inserted through the cannula and advanced to the target site. In some embodiments, the probe 100 can be inserted directly to the target tissue and may include a sharp trocar tip at a distal end of the probe. In one such example, the target tissue is a soft tissue. In another embodiment, a bilateral approach may be used to treat a vertebral body. The probe 100 may be inserted into a vertebral body at a first target location to the right of the mid-saggital plane at an angle of about 15 to about 25 degrees to the mid-saggital plane. A first bi-polar lesion may then be formed at a first location within the vertebral body. The probe 100 may then be inserted at a second target location to the left of the mid-saggital plane at an angle of about 15 to about 25 degrees from the mid-saggital plane. A second bi-polar lesion may then be formed at a second location within the vertebral body. In one such example, the first and second lesions may encompass a majority of the vertebral body.

Bipolar lesions of different geometry can be created by manipulating the duration and intensity energy delivered through each electrode as the control electrode. This is related to the higher tissue temperatures being found around the control electrode. Manipulating a bipolar probe can create lesions that are peanut, mushroom or symmetric ellipsoid shaped. Keeping each electrode active for 50 percent of the time can help in creating symmetrical or more symmetrical lesions.

In one example, RF energy is supplied by an RF generator in a bipolar manner to probe 100. The power output of the RF generator may be temperature controlled. In one embodiment, direct tissue temperature monitoring is used in conjunction with internal cooling when supplying RF power to form a lesion. The power output may be adjusted based on the measured temperature response of the tissue to RF heating under cooling. The temperature response of the target tissue may be monitored using the temperature sensor 80.

One embodiment is for a system in which the user puts the selected coolant temperature into the system from a range from just above 0 degrees C. up to about 30 degrees C. The cooling fluid is delivered by a pump unit, which is controlled by the same generator that delivers energy. The flow rate (and correspondingly the amount of cooling) can be adjusted based on tissue characteristics and the intended lesion geometry.

The RF energy is delivered in a bipolar manner between conductors 30 and 50 and allows a lesion 90 to be formed adjacent the active tip 70. Three factors in controlling lesion size and shape (lesion geometry) are temperature, time of procedure and active tip geometry which includes length of the active tip segments and ratios of the segments lengths. In one example the active tip 70 has a length of about 20 mm, and the distal electrode 32, the exposed inner insulator 40 and the proximal electrode 52, have a length ratio L1:L2:L3 of about 7:6:7. A ramp rate of about 10° C./min is used in order to reach a set temperature of about 65° C. to about 70° C. The power is supplied for about 15 minutes, resulting in a lesion having a size of about 30 mm×23 mm, with a lesion volume of about 8.3 cm$^3$.

In another example an active tip 70 with a length of about 30 mm is used, and the distal electrode 32, the exposed inner insulator 40, and the proximal electrode 52 have a length ratio L1:L2:L3 of about 1:1:1. A ramp rate of about 20° C./min may be used. In one instance of this example, the ramp rate may be used to achieve a set temperature of about 100° C. The power is supplied for about 20 minutes, resulting in a lesion size of about 45 mm×35 mm, with a lesion volume of about 28.9 cm$^3$.

In yet another example, a ramp rate of about 40° C./min is used to achieve a set temperature of about 90° C. Power is applied for about 5 minutes, resulting in a lesion size of about 15 mm×15 mm with a volume of about 1.8 cm$^3$. In some embodiments, the tissue temperature may be maintained at between about 40 degrees and about 100 degrees.

In some cases, the predictability of lesioning is improved by the use of external monitoring electrodes. For example, placing a monitoring electrode at the periphery of a centrally-formed lesion can help a physician decide when to stop lesioning to ensure an adequate size or the monitoring electrode could be in communication with a generator with a control program that controls energy delivery. The output of a generator could be controlled by one or more monitoring electrode such as temperature monitoring electrodes. One example includes placing at least one external temperature sensor at the boundary of a desired lesion, monitoring the at least one external temperature sensor during energy delivery, and determining the lesion is complete when the external temperature reaches a predefined value.

In some embodiments, the power may be delivered at from about 1 Watt to about 100 Watts. In another example power may be delivered at from about 1 Watt to about 50 Watts. In other embodiments, greater than 100 Watts of power may be delivered by the RF energy delivery source. In still another embodiment, less than 1 Watt of power may be delivered. In some embodiments power may be delivered for a duration of between about 2 minutes to about 30 minutes. In other embodiments power may be applied for less than 2 minutes or greater than 30 minutes.

In some embodiments, the ramp rate may range from about 2° C./min to about 100° C./min. In one example, the ramp rate may be about 10° C./min. In another example, ramp rate may be about 20° C./min. In still another example, ramp rate may be about 40° C./min. In one embodiment the rap rate may be set to optimize the tissue response to achieve the set temperature. This may prevent charring, desiccation or vaporization of tissue. In some embodiments, the power supplied to the bipolar coaxial probe 100 may be less than power supplied to a monopolar probe to achieve as equivalent lesion.

Thus, as described hereinabove, an electrosurgical probe with internal cooling can be particularly useful, for example, in systems and methods for lesioning in bone and other tissue. In some embodiments, the probe is comprised of at least two electrically isolated electrical conductors which are operable to deliver energy in a bipolar manner. One embodiment of such a probe includes an inner conductor inside an outer conductor. The inner electrical conductor includes a lumen for the internal circulation of a cooling fluid. The probe also has an electrical insulator layer between the inner and outer electrical conductors for electrically isolating the electrical conductors. The electrical insulator has sufficient thermal conductivity to allow for cooling of the outside electrical conductor by cooling fluid circulating within the lumen of the inner electrical conductor. Thus, only one conductor is cooled directly, i.e. with contact of the cooling fluid, while the other conductor is indirectly cooled. When used in a system, the probe could enable temperature monitoring to provide data for controlling the delivery of energy through electrodes to tissue and for controlling the flow of cooling fluids to the electrodes.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of treating pain generated by nervous tissue at an interface between bone of a vertebral body and a tumor located at least partially within the vertebral body, the method comprising:

delivering energy to the nervous tissue using a single bipolar probe having an active tip comprising at least two electrodes, the at least two electrodes including at least a generally tubular outer electrode defining a first lumen having a longitudinal axis, and a generally tubular inner electrode defining a second lumen having a longitudinal axis extending coaxially with the longitudinal axis of the first lumen along at least a portion of the outer electrode, the energy being sufficient to limit generation of pain signals by the nervous tissue; and cooling the outer electrode and the inner electrode by flowing a coolant within the second lumen of the inner electrode as the energy is being delivered to the nervous tissue to limit charring of the tissue at the surface of the at least two electrodes.

2. The method of claim 1 further comprising monitoring the temperature of the nervous tissue to which the energy is being delivered, and controlling the delivering energy in response to the temperature.

3. The method of claim 1 further comprising advancing the active tip into a trabecular bone.

4. The method of claim 1 further comprising using an introducer assembly, comprising a cannula with a stylet disposed therein, to advance the single bipolar probe into the vertebral body, and wherein the stylet is withdrawn from the cannula subsequent to the introducer assembly being advanced into the vertebral body.

5. The method of claim 4 further comprising inserting the introducer assembly into the vertebral body using a transpedicular approach.

6. The method of claim 1, wherein the delivering energy to the nervous tissue using the single bipolar probe further comprises using the single bipolar probe having an electrically-exposed outer conductor at a distal end of the outer electrode.

7. The method of claim 1, wherein the flowing of the coolant within the second lumen includes circulating the coolant within the second lumen between a coolant supply provided at a proximal end thereof, and a closed distal end thereof.

8. The method of claim 1, wherein the first lumen has a first length, and the second lumen has a second length, the second length being different from the first length.

* * * * *